United States Patent
Mottram

[11] Patent Number: 5,972,840
[45] Date of Patent: Oct. 26, 1999

[54] OSMOLYTE REGULATOR

[75] Inventor: Malcolm Mottram, Romsey, Australia

[73] Assignee: AB Tall (Holdings) Pty. Ltd., Australia

[21] Appl. No.: 08/875,630

[22] PCT Filed: Feb. 2, 1997

[86] PCT No.: PCT/AU96/00045

§ 371 Date: Oct. 1, 1997

§ 102(e) Date: Oct. 1, 1997

[87] PCT Pub. No.: WO96/23413

PCT Pub. Date: Aug. 8, 1996

[30] Foreign Application Priority Data

Feb. 2, 1995 [AU] Australia .................. PN0853

[51] Int. Cl.$^6$ .......... A01N 61/00; A01N 37/44; A01N 33/12; A01N 43/72
[52] U.S. Cl. .......... 504/244; 504/248; 504/283; 504/319; 504/320; 504/345
[58] Field of Search .......... 504/244, 248, 504/283, 319, 320, 345

[56] References Cited

FOREIGN PATENT DOCUMENTS

| | | |
|---|---|---|
| 0 373 314 | 6/1990 | European Pat. Off. . |
| 259 123 A1 | 8/1988 | Germany . |
| 277 832 | 4/1990 | Germany . |
| 277 833 A1 | 4/1990 | Germany . |
| WO 93/17556 | 9/1993 | WIPO . |
| WO 95/28836 | 11/1995 | WIPO . |

OTHER PUBLICATIONS

Derwent Abstract Accession No. 95–183638/24, class C02, RU 2020822–C1 (As Mold Genetics Inst), Oct. 15, 1994 abstract.

Chemical Abstracts, vol. 123, No. 5 issued Jul. 1995 Hanson et al "Replacement of glycine etaine by α–alanine betaine . . . " p. 549, col. 1, abstract No. 52227g, NATO AS1 ser., ser. 1 1993, 593–601.

Phytochemistry, vol. 30, No. 2, issued 1991 Naidu et al "Amino acid and glycine betaine accumulation in cold–stressed wheat seedlings" p. 407–409.

Current Science, vol. 59, No. 2 Jan. 1990 Krishnamurthy et al "Accumulation of choline and glycine betaine in salt stressed wheat seedlings", p. 111–112.

Derwent Abstract Accession No. 89–104862/14 class C02, JP 01052703A Nippon Zoki Pharm KK Feb. 1989 Abstract.

Plant Physiology, vol. 97 1991, Hanson et al "Comparative physiological evidence that α–alanine betaine and choline–O–sulfate . . . " p. 1199–1205.

Samorodov et al. CA 104:83680 Abstract of "Stimultaion of fruit set and parthenocarpy in pears by proline and gibberellin treatment of flowers injured by frosts" Dopov. Akad. Nauk. Ukr. RSR, Ser. B. 12:55–58, 1985.

Nolte et al. Agricola abstract 1998:26471 of "Proline accumulation and methylation to proline betaine in Citrus: implications for genetic enginerring of stress resistance." J. Am. Soc. Horticultural Sci. 122(1):8–13, Jan. 1997.

Primary Examiner—S. Mark Clardy
Attorney, Agent, or Firm—Nixon & Vanderhye

[57] ABSTRACT

A treatment for relieving or combating stress in a plant before harvesting is described in which an amount of an osmolyte regulator is applied to the plant at a predetermined time before harvesting so as to prevent or reduce blemishes or damage of the skin of the plant. The treatment may be applied to a diverse range of plants such as pears, peaches, cherries and similar fruit, and tropical fruits and nuts. A preferred osmolyte regulator is glycine betaine or other betaine derivatives, and the preferred dosage rate is up to 20,000 ppm in aqueous solution with or without other additives. The osmolyte regulator is applied to the plants by spraying the leaves. Other osmolyte regulators are compounds such as N-methyl substituted amino acids, proline, or choline, stachydrine, trigonelline, and homostachydrine, glycine, glutamic acid, GABA, trimethylamine, or butyric acid.

29 Claims, 1 Drawing Sheet

Fig.1

OSMOLYTE REGULATOR

This application has been filed under 35 USC 371 as the National Stage application International application PCT/AU96/00045, filed Feb. 2, 1996.

The present invention relates generally to agriculture and in particular to methods of improving or controlling the growth of crops. More particularly, the present invention relates to methods of controlling stress and related conditions in plants during the growth of the plant, particularly in the early stages of growth and more particularly where the plant is pear, peach, cherries or the like. Even more particularly, the present invention relates to the use of an osmolyte regulator, particularly glycine betaine, to control stress in growing cherries so as to prevent the development of cracking in the skins and like areas of the cherries, thereby increasing the value of the cherry crop. The present invention finds particular application in administering glycine betaine to cherries by spraying at predetermined times to reduce or eliminate the number of cherry fruits which develop cracks in their skins.

BACKGROUND OF THE INVENTION

Although the present invention will be described with particular reference to the use of glycine betaine as one example of the osmolyte regulator administered to cherry plants to control stress in the plants, particularly the tendency of the skins of the cherries to crack, it is to be noted that the scope of the present invention is not restricted to the described embodiment but rather the present invention is more extensive so as to include the use of other osmolyte regulators, to other ways of administering the regulators, and to other uses of the chemical compounds than as osmolyte regulators, and to the use of the regulators on crops other than those specifically described, particularly on pears, peaches and the like.

Cherries are a crop having considerable economic value. As cherries grow they are often subjected to stress in one or more forms. The cherries respond to stress by cracking their skins. Consequently, the development of stress within the cherries is easily and readily observable and demonstrable. The amount of cracking developed by the cherries is an indication of the amount of stress to which the cherries are being subjected. The main causes of skin cracking include too much or too little water, inadequate nutrition, low light intensity, low temperatures, and the like.

Cracks usually develop in cherries during the latter stages of ripening of the cherries and cracking is more severe under wetter conditions than under drier conditions. It is believed that cracking is caused by a build up of pressure within the fruit so that the skin is not strong enough to withstand the increase in pressure without splitting.

The development of cracks in the skin of ripe cherries reduces the economic worth of the crop since cherries with cracked skins cannot be sold at a premium price as high quality table fruit, but rather can only be used in lower quality applications, such as for example in making jams and the like, which lower quality applications do not produce the same economic returns to the growers as when the cherries are sold as high quality table fruit. Additionally owing to the cracking of the skins secondary infection such as for example by moulds, brown rot, fungi and other pathogens can infect and develop within the cherries, so that a majority of cracked fruit is often not suitable for any purpose and is simply dumped. Therefore, any reduction in the amount or extent of cracking in cherries will be beneficial to the grower as the fruit will be of a more uniform high quality and demand higher prices when sold, which increases the economic value of the crop and the monetary return to the grower.

The same applies to many other types of fruit such as for example, pears, peaches and the like.

Therefore, it is an aim of the present invention to provide a method of administering an osmolyte regulator to a plant, particularly to cherry plants for controlling the stress induced or developed in the growing plant so as to overcome or at least reduce the tendency of the skins of the plant to crack, particularly during ripening.

DESCRIPTION OF THE INVENTION

According to one aspect of the present invention there is provided a method of controlling stress in a growing plant to reduce surface imperfections of the skin of the plant comprising administering an effective amount of an osmolyte regulator to the plant such that stress induced or developing in the plant can be controlled to a satisfactory level in order to enhance the growth of the plant by eliminating or reducing the amount of surface imperfection, blemish or damage so as to provide a greater yield of the plant at a higher quality of product.

Typically, the plant to which the osmolyte regulator of the present invention can be administered includes peaches, apricots, nectarines, pears, stone and pome fruit generally, citrus fruit and the like, particularly including cherries. Typically the plant to which the osmolyte regulator of the present invention can be administered includes tropical fruits and nuts such as bananas, mangoes, macadamias and almonds. More typically, the cherries can be of any species and are preferably the Stellar variety.

Typically, the osmnolyte regulator is an organic solute, a compatible solute, an amino acid, a betaine, a sugar, a polyol, or related compounds to the foregoing, and the like. More typically, the osmolyte regulator is an ammonio compound, such as a n-methyl substituted amino acid, proline, choline or a betaine, such as glycine betaine (oxyneurin) and other betaine member compounds and the sulphonio analogues of the betaines. Other betaines include proline betaine, β-alanine betaine, tryptophan betaine, histidine betaine, 2-mercaptohistidine betaine, and the like. Even more typically, the osmolyte regulator is a nitrogenous compatible solute, such as stachydrine, trigonelline, homostachydrine (pipecolate betaine).

Other osmolytes or oemoregulators include glycine, methylene glycine, dimethyl glycine, glutamic acid, γ-aminobutyric acid, trimethylamine γ-butyric acid, or the like.

Typically, the osmolyte regulator is administered alone or in combination with one or more other materials, such as adjuvants. Typically, the other materials include additives such as wetting agents, defoliants, growth regulators, pesticides, fungicides, vegetable and mineral oils, nutrients and the like. The other materials can be added separately or in combination to the osmolyte regulator. Even more typically, the osmolyte regulator and other materials if present have a synergistically beneficial effect on the plant.

Typically, the amount of osmolyte, typically glycine betaine, administered to the growing plant is such so as to reduce or eliminate the tendency of the plant to develop surface irregularities, imperfections, blemishes, damage or the like, including cracks in the skin as they ripen, thus increasing the economic worth of the crop of cherries.

Typically, the stress induced or developed in the cherries includes environmental stresses such as, for example, stress related to temperature, water, salinity, light, nutritional stresses and the like. More typically, the stress induced results from too little or too much water, too low a temperature, too high a salt concentration, too low a light intensity, too low nitrogen concentration, and the like.

Typically, the glycine betaine is administered to the cherries in a concentration of up to about 20,000 ppm, preferably up to about 10,000 ppm, more preferably from 1000 to 10,000 ppm, most preferably 3,000 to 10,000 ppm. The dosage rate of glycine betaine administered to the plants typically is in the range of up to 100 kg/100 L preferably up to 5 kg/100 L, more preferably up to 2.5 kg/100 L, most preferably from about 0.1 to 1 kg/100 L of glycine betaine in aqueous solution.

Typically, the regulator either alone or in combination with the other materials is applied to the leaves and fruit of the cherry plants, more typically as an aqueous solution.

Typically, the osmolyte regulator can be applied to the crops at any time, preferably late in the life of the crops, typically shortly before the crops ripen, more typically just before the fruit is ready for harvesting. More preferably the glycine betaine is applied at a time from when about 30% to 40% of the cherries are pink to red fruit to when about 70% to 80% of the cherries are pink to red fruit. More typically, the glycine betaine is applied to the cherries to the point of runoff. Dose rate is related to canopy size and thus the term "dose" is referred to as "to the point of runoff". This means the point when the leaves are covered by the solution and excess begins to run off.

It is to be noted that the osmolyte regulator can be administered to the plants at any time until harvesting, including before, during or after flowering of the plants, development of fruit, ripening of the fruit and the like. It is further to be noted that there can be a single administration of the osmolyte regulator or it may be administered in two, three, four or more separate applications.

Typically, the osmolyte regulator is applied to the plants by spraying, more typically spraying of aqueous solution. However, the osmolyte regulator may be applied in any suitable manner.

Typically, the more advanced the fruit form of the plant when the osmolyte regulator is applied, the more the plant responds to the addition of the osmolyte regulator, and more control over stress induced in the plant is obtained. More typically, the proportion of individual cherries having cracked skin decreased with an increase in fruit size when the glycine betaine is administered. Increasing the dose of glycine betaine significantly reduces the proportion of cracked fruit and the effectiveness of treatment with glycine betaine increased with the maturity of the fruit.

The present invention will now be described by way of example with reference to the following examples.

EXAMPLE 1

The object of this example is to determine the effect of foliar applications of glycine betaine on the tendency of cherries to crack during ripening. The variety of cherries used in the following trial is Stellar. The cherry trees were mature trees about 15 years old and planted on a 5.5 m by 6.0 m grid having a shape described as "delayed-modified central leader". The dimensions of the plants were 4.5 to 5.5 m high by 4.5 to 5.0 m in diameter of from 70 to 110 cubic metres with moderate foliage density.

Layout of the Trial

The layout of the trial included the following details:

design: randomised complete block replications: 4 plot size: single tree butters: nil

Treatments

Details of the treatments included the following:

| Code | Active ingredient | Dose active ppm |
|---|---|---|
| A | glycine betaine | 1000 |
| B | glycine betaine | 3000 |
| C | glycine betaine | 6000 |
| D | glycine betaine | 1000 |
| E | glycine betaine | 3000 |
| F | glycine betaine | 6000 |
| G | | untreated control |

Application

The equipment used to apply the treatments to the cherry plants included a hand-held spray gun fitted with a single nozzle on a 1 m long extension.

Application Treatments

| Application No. | 1 | 2 |
|---|---|---|
| Treatments Applied | A. B. C. | D.E.F |
| Day No. | 0 | 10 |
| Time | 0715 to 0810 | 1935 to 2040 |
| Nozzle Designation | 1/4 GG 3009 | |
| Nozzle Manufacturer | Spraying Systems Co. | |
| Pressure at Nozzle (kPa) | 1900 | |
| Droplet Size | medium spray | |
| Spray Volume. (Vha) | to point of runoff: 9 to 12 Inree e. | 110 to 130 liters per 1000 cubic meters of plant volume. |
| Temperature (° C.) | 19 | 25 |
| $\Delta T$ (° C.) | 2 | 1 (orchard recently irrgated) |
| Relative Humidity (%) | 85 | 92 |
| Wind Speed (m/sec) | nil | nil |
| Wind Direction | n/a | n/a |
| Cloud Cover | 90 to 100% | 70 to 80% |

-continued

| Application No. | 1 | 2 |
|---|---|---|
| Spray Drift | v low | very low |
| Foliage Condition | dry | dry |
| Spray Drying Time | 1 to 15 hours | more than 1.5 hours |
| Crop Stage | Fruit to 22 m in diameter. 83% Dark Green. 16% Light Green., 1% Pink. | Fruit to 25 mm in diameter. 11% Dark green. 64% Light green. 19% Pink, 6% Red |
| Crop Condition | Healthy, vigorous No stress or disease evident. Very light infestation of *Caliroa cerasi*. No cracking observed. | |

Inspection and Assessment

Inspection of the fruit of the cherry plants under test for colour development was carried out at 3 and 8 days after the first treatment application, which was denoted to be day 0, just before the second treatment application, which occurred at day 10, and two days after the second application, in order to determine the appropriate time to start the assessments.

At 13 days after the first application and 3 days after the second application two samples of 200 fruit per tree were examined. The first sample consisted of the 10 fruit nearest the point 0.5 metres down from the tip of each of 20 branches. The branches selected were as evenly spaced around the tree as possible. The number of fruit that were more than 50% red were recorded as well as the number showing symptoms of phytotoxicity which is typically seen as a discoloured area at the drip point which is surrounded by a prominent band of darker coloured tissue.

The second sample consisted of 10 fruit each more than 50% red on each of 20 branches per tree. The branches selected were as evenly spaced around the tree as possible. The number of cracked fruit from each sample was recorded.

To ensure that classification of colour was constant, each of the two assessors frequently referred to examples of each classification selected before the assessment began.

At 16 days after the first application the proportion of red fruit was estimated again, using the same sampling procedure as at 13 days.

At 20 days after the first application, 15 fruit on each of 20 limbs per tree were examined and the numbers with cracks and symptoms of phytotoxicity were recorded. At this time virtually all fruit were red.

Results

The results of the trial are summarised in Table 1.

Fruit Colour

Compared with the untreated control (treatment g), none of the treatments (A, B, C, D, E, F) had any significant effect ($p>0.7$) on the proportion of red fruit that had developed at either assessment. This suggests that it was most unlikely that the glycine betaine treatments affected the maturation of the cherries and accordingly the yield of cherries was not significantly altered by the administration of the glycine betaine. However, the glycine betaine may assist in some way which was not readily observable in the actual trial being conducted.

Cracking

The frequency of cracking in this trial was moderate, and also the severity of cracking was very light with cracks ranging from 1 mm to 3 mm in length and penetrating to a depth of no more than 1 mm.

The application of glycine betaine at 6000 ppm (treatment c) to predominantly dark green fruit had no significant ($p>0.05$) effect on the proportion of fruit which developed cracks at the time of harvest. But later application (treatment f) of this same dose to predominantly light green fruit significantly ($p<0.05$) reduced the proportion of fruit which developed cracks by 65%. At both times of application, the lower doses of glycine betaine tested, 1000 and 3000 ppm respectively, had no significant effect on the proportion of fruit that was cracked at harvest. However, the trends in the results suggest that doses lower than 6000 ppm may be effective, particularly if such doses are applied at later times closer to harvest than at the timing used in this trial. Also at both assessments of the effects of the later application the proportion of cracked fruit was highly correlated with the dose of glycine betaine, i.e. first assessment: $r=0.6803$, $P<0.010$, $n=12$; second assessment: $r=0.7623$, $p<0.001$, $n=12$.

Cracks usually develop in cherries during the latter stages of ripening and cracking is more severe under wetter conditions than under drier conditions. All assessments of cracking were made on the ripest (red) fruit and as a result the samples used for the first and second assessments were comprised of different fruit. This explains the significant difference in the proportion of cracked fruit between the first and second assessments viz. an average of 19.1% cracked fruit at the first assessment and 15.3% at the second assessment ($p=0.037$, paired t-test).

Conclusions

The effectiveness of foliar applications of glycine betaine in reducing the proportion of cracked cherries increased with increasing dose and with the maturity of the fruit at the time of application of the glycine betaine. While only the highest dose at the latest time of application (6000 ppm, at 10 days before harvest) was significantly ($p<0.05$) effective in this trial, the trends in the results of other doses and other times of application suggested that lower doses are effective if applied at later times closer to the time of actual harvest.

The level of performance of the most effective treatment, which was a dosage of 6000 ppm at day 20, showing a 65% is reduction in the amount of cracked cherries, is more than sufficient for commercial utility. Table 2 shows the actual number of fruit which were assessed as being cracked for each of the treatments. Treatments 1 to 7 correspond to treatments A to G. The data relating to the actual number of fruit with cracks was used to calculate the results shown in Table 1.

TABLE 1

| TREATMENT | | | Mean % Red *1 Fruit | | Mean % Fruit *1 with symptoms of phytotoxicity | | | Mean % Red fruit *1 with cracks | | |
|---|---|---|---|---|---|---|---|---|---|---|
| Code | Dose of Betaine Glycine (ppm) | Date Applied | Day 13 | Day 16 | Day 13 *2 | | Day 20 | Day 13 | Day 20 *3 | |
| 1 | 1000 | Day 0 | 16.5 | 51.4 | 11.2 | b | 0.2 | 22.6 | 15.7 | bcd |
| 2 | 3000 | Day 0 | 17.1 | 58.3 | 11.7 | b | 0.3 | 14.8 | 19.9 | cd |
| 3 | 6000 | Day 0 | 19.3 | 57.7 | 13.9 | b | 0.2 | 21.9 | 12.2 | abc |
| 4 | 1000 | Day 10 | 14.9 | 57.9 | 12.7 | b | 0.4 | 26.6 | 23.6 | d |
| 5 | 3000 | Day 10 | 14.2 | 55.7 | 14.5 | b | 0.5 | 14.4 | 10.7 | ab |
| 6 | 6000 | Day 10 | 15.6 | 53.9 | 12.8 | b | 0.2 | 8.6 | 5.9 | a |
| 7 | Untreated Control (UTC) | | 16.5 | 57.0 | 0.0 | a | 0.0 | 21.1 | 17.0 | bcd |
| F (prob.) 2 way ANOVA | UTC Out | | 0.797 | 0.724 | 0.951 | | 0.858 | 0.147 | 0.003 | |
| | UTC In | | 0.865 | 0.965 | <0.001 | | 0.560 | 0.129 | 0.006 | |

*1 All means de-transformed from angles.
*2 Letters indicate statistical separation (p = 0.05). Fishers protected LSD test
*3 Statistical separation the same with control included or excluded.

A discussion of the results of Table 1 will now follow.

As can be seen from the results of Table 1, particularly from the results of the column headed "Mean % red fruit with cracks", when treatment F (corresponding to code 6) is considered there is a reduction of from 21.1% of fruit with cracks from treatment 7 (G) resulting from the controlled untreated treatment to 8.6% after 13 days. This means that within 3 days after application of the glycine betaine there was observed an improvement in the reduction of cracked fruit.

TABLE 2

| TRT. Code | Applcn. Time | Plot/Tree No. | Row No. | Rep. | No of Cracked Fruit | | No. of Red Fruit | | No. of Fruit with symptoms of phytotoxicity | |
|---|---|---|---|---|---|---|---|---|---|---|
| | | | | | Day 13 per 200 Red Fruit | Day 20 per 300 Fruit | Day 13 per 200 Fruit | Day 16 per 200 Fruit | Day 13 per 200 Fruit | Day 20 per 300 Fruit |
| 1 | 1 | 2 | 1 | 1 | 71 | 53 | 52 | 125 | 16 | 1 |
| 1 | 1 | 22 | 2 | 2 | 31 | 63 | 33 | 102 | 32 | 0 |
| 1 | 1 | 9 | 1 | 3 | 62 | 47 | 31 | 87 | 35 | 2 |
| 1 | 1 | 13 | 1 | 4 | 23 | 29 | 19 | 97 | 8 | 0 |
| 2 | 1 | 26 | 2 | 1 | 34 | 72 | 50 | 156 | 17 | 1 |
| 2 | 1 | 7 | 1 | 2 | 37 | 39 | 41 | 107 | 34 | 1 |
| 2 | 1 | 18 | 2 | 3 | 23 | 82 | 33 | 111 | 33 | 2 |
| 2 | 1 | 14 | 1 | 4 | 25 | 50 | 17 | 89 | 10 | 0 |
| 3 | 1 | 28 | 2 | 1 | 24 | 51 | 32 | 141 | 35 | 1 |
| 3 | 1 | 23 | 2 | 2 | 81 | 42 | 46 | 123 | 23 | 0 |
| 3 | 1 | 20 | 2 | 3 | 60 | 17 | 39 | 104 | 28 | 1 |
| 3 | 1 | 12 | 1 | 4 | 20 | 41 | 38 | 93 | 22 | 0 |
| 4 | 2 | 4 | 1 | 1 | 57 | 67 | 35 | 131 | 24 | 1 |
| 4 | 2 | 6 | 1 | 2 | 76 | 91 | 25 | 103 | 27 | 2 |
| 4 | 2 | 21 | 2 | 3 | 21 | 34 | 45 | 119 | 19 | 1 |
| 4 | 2 | 11 | 1 | 4 | 66 | 99 | 17 | 92 | 28 | 1 |
| 5 | 2 | 1 | 1 | 1 | 24 | 26 | 19 | 84 | 13 | 9 |
| 5 | 2 | 24 | 2 | 2 | 38 | 37 | 27 | 145 | 41 | 0 |
| 5 | 2 | 8 | 1 | 3 | 23 | 23 | 43 | 132 | 25 | 0 |
| 5 | 2 | 16 | 2 | 4 | 31 | 45 | 27 | 100 | 31 | 1 |
| 6 | 2 | 27 | 2 | 1 | 5 | 8 | 31 | 97 | 32 | 0 |
| 6 | 2 | 25 | 2 | 2 | 18 | 26 | 23 | 127 | 30 | 2 |
| 6 | 2 | 10 | 1 | 3 | 15 | 22 | 33 | 93 | 17 | 0 |
| 6 | 2 | 17 | 2 | 4 | 38 | 18 | 39 | 114 | 21 | 1 |
| 7 | n/a | 3 | 1 | 1 | 35 | 45 | 45 | 127 | 0 | 0 |
| 7 | n/a | 5 | 1 | 2 | 41 | 48 | 21 | 98 | 0 | 0 |
| 7 | n/a | 19 | 2 | 3 | 51 | 51 | 33 | 96 | 0 | 0 |
| 7 | n/a | 15 | 2 | 4 | 42 | 61 | 33 | 134 | 0 | 0 |

At 20 days after application, the percentage of cherries with cracks resulting from treatment 6 was 5.9% as compared to the untreated fruit which exhibited 17.0% of the fruit with cracks.

Thus, with larger dosages of treatments of glycine betaine such as at 6000 ppm at a later timing of application closer to harvest time, it can be seen that a greater proportion of the cherry crop was free from cracking and hence of greater economic value to the grower.

EXAMPLE 2

The object to this example was to determine the effect of dose and time of application on the effectiveness of foliar sprays of glycine betaine in preventing cracking in cherries. The variety of cherry is Stellar and the age of the trees is about 20 years with the trees planted on a 6 m by 6 m grid. The tress have modified central leader shape. The dimensions of the plants were 5–6 m in height by 5–6 m in diameter, or from 80 to 130 cubic metres, with a moderate to high foliage density.

The trial was laid out as a randomised complete block experiment with 4 blocks, each containing one replicate of each treatment. The plot size was one tree.

| Code | Material | Dose | Time of application |
|---|---|---|---|
| A | glycine betaine | 3000 | 30% to 40% pink to red fruit. Timing 1 (T1) |
| B | | 6000 | |
| C | | 10000 | |
| D | glycine betaine | 3000 | 70% to 80% pink to red fruit. Timing 2 (T2) |
| E | | 6000 | |
| F | | 10000 | |
| G | untreated control | | |

MONSOON, an aqueous solution containing 300 g/L linear (C9 to C11) alcohol ethylene oxide condensate, was added to all sprays at 30 mL/100 L.

The equipment used to apply the treatments to the cherry plants under test included a hand-held spray gun fitted with a single nozzle, on a 1 m long extension.

Timing and Conditions of Application of Treatment

| Application No. | 1 | 2 |
|---|---|---|
| Treatment applied | A, B, C | D, E, F |
| Day No. | 0 | 8 |
| Time | 19.15 to 20.55 | 19.30 to 20.45 |
| Nozzle designation | ¼ GG 3009 | |
| Nozzle manufacturer | Spraying Systems Co | |
| Pressure at nozzle (kpa) | 1700 | |
| Droplet size | Medium spray | |
| Spray volume (l/ha) | Trees sprayed to the point of runoff: 9 to 16 L/tree - equivalent to 105 to 120 liters per 1000 cubic meters of plant volume. | |
| Temperature (°C.) | 19 to 21 | 20 to 22 |
| Relative humidity (%) | 80 to 85 | 65 to 75 |
| Wind Speed (m/sec) | Nil; dead calm | |
| Cloud cover | 60 to 80% | 50 to 80% |
| Spray drift | Negligible due to wind, but where foliage of adjacent trees contacted each other, treatment of non-target tree was unavoidable. | |
| Foliage condition | Dry | |
| Spray drying time (hour) | >1 | |
| Crop stage | refer assessments | |
| Crop condition | Healthy, vigorous, no stress or pests evident. Very heavy fruit load. | |

Inspection and Assessments

The circumference of all trees at 0.3 m above the soil (butt circumference) was measured when the trial was pegged out.

To estimate the proportion of pink/red fruit at application, 5 groups of 10 fruit were examined on each tree to be sprayed and on each untreated control tree. This was repeated at the second application timing.

Fifty dark red (ripe) fruit were picked from the shoulder height circumference of the canopy of each tree. Fruit were not sampled from areas where the foliage contacted that of adjacent trees. After the samples were immersed for ca 20 hours in de-ionized water at 17 to 22° C., each fruit was examined and classified as either sound or cracked. On the last occasion, the volume of each sample of 50 fruit was measured.

The results of this example are provided in Table 3. Cracking was artificially induced by immersing fruit in water because virtually none of the fruit on the tress had cracked due to the prevailing weather conditions at the time that the trials of this example were conducted.

When the data was analysed according to the original design, no statistically significant ($p<0.05$) responses were obtained (Table 3).

TABLE 3

Initial analysis of results

| TREATMENT | | | Mean | | | | |
|---|---|---|---|---|---|---|---|
| | Dose of GB | Time of | Butt | Mean % Pink/Red Fruit | | Mean % Cracked Cherries | |
| Code | (ppm) | Appln | Circum (cm) | T1 | T2 | As. 1 | As. 2 |
| A | 3000 | T1 | 85 | 34 | 81 | 37 | 37 |
| B | 6000 | T1 | 77 | 33 | 81 | 27 | 36 |
| C | 10000 | T1 | 77 | 33 | 83 | 23 | 23 |
| D | 3000 | T2 | 80 | 40 | 81 | 26 | 30 |
| E | 6000 | T2 | 74 | 43 | 77 | 19 | 29 |
| F | 10000 | T2 | 80 | 37 | 75 | 18 | 18 |
| G | Untreated control | | 76 | 42 | 75 | 25 | 36 |
| 1-way ANOVA F | | | 0.932 | 0.713 | 0.289 | 0.736 | 1.273 |
| prob. | | | 0.496 | 0.664 | 0.934 | 0.628 | 0.318 |

*1 Analyses calculated using original spatial blocking.

Further examination of the data showed that with fruit from untreated controls, the proportion of cracked fruit increased with an increase in fruit size (volume). However, with fruit from glycine betaine treated trees, the proportion of cracked fruit decreased with an increase in fruit size (Table 4).

TABLE 4

Interaction between fruit size (volume) and
treatment on the proportion of cracked fruit

| | TREATMENT | | Linear regression of % cracked fruit on volume of 50 Fruit (n = 24) | | | | Mean of both | |
|---|---|---|---|---|---|---|---|---|
| | Dose | Time | Assessment 1 | | Assessment 2 | | Assessments | |
| Code | of GB (ppm) | of Appln | Slope | Sig. level | Slope | Sig. level | Slope | Sig. level |
| A | 3000 | T1 | −0.259 | 0.051 | −0.436 | 0.023 | −0.347 | 0.030 |
| B | 6000 | T1 | −0.264 | 0.049 | −0.187 | >0.001 | −0.226 | 0.007 |
| C | 10000 | T1 | −0.281 | 0.131 | −0.290 | 0.007 | −0.289 | 0.027 |
| D | 3000 | T2 | −0.455 | 0.004 | −0.390 | 0.004 | −0.423 | 0.004 |
| E | 6000 | T2 | −0.136 | 0.130 | −0.348 | 0.007 | −0.242 | 0.027 |
| F | 10000 | T2 | −0.038 | 0.285 | −0.124 | 0.118 | −0.081 | 0.135 |
| G | 0 | n/a | 0.107 | 0.018 | 0.177 | 0.015 | 0.142 | 0.016 |

Since the responses to fruit size were opposed as indicated by the different directions of the slopes shown in Table 4, the glycine betaine data and the untreated control data were analysed separately. Additionally, the glycine betaine data was re-blocked on the basis of fruit size to allow for the response to this variable. This analysis showed (Table 5) that increasing the dose of glycine betaine applied to the fruit significantly reduced the proportion of cracked fruit and that the effectiveness of glycine betaine treatments increased with the maturity of the fruit, which is to say that the more mature the fruit when the glycine betaine is applied, the more effective is the treatment. Since the results of the two assessments were highly correlated (R sqrd=0.7307, p<0.001), the analyses were also calculated for pooled data.

TABLE 5

Analyses of data blocked on the basis of
fruit size (volume)

| | | | Mean % cracked fruit (detransformed from angles) Assessment Number | | |
|---|---|---|---|---|---|
| | Dose of | Time of | | | |
| Code | GB (ppm) | Appln | 1 | 2 | 1 & 2 |
| A | 3000 | T1 | 37 b *1 | 37 c | 37 c |
| B | 6000 | T1 | 27 ab | 36 c | 32 bc |
| C | 10000 | T1 | 23 a | 23 ab | 23 ab |
| D | 3000 | T2 | 26 ab | 30 bc | 28 bc |
| E | 6000 | T2 | 19 a | 29 abc | 24 ab |
| F | 10000 | T2 | 18 a | 18 a | 18 a |
| F (prob.) 2-way ANOVA | | | 0.050 | 0.026 | 0.018 |
| G *2 | Untreated Control | | 25 | 36 | 31 |
| Fruit Size-Block means: GB treatments only | | | | | |
| Size 1 | smallest | | 38 b | 48 c | 43 c |
| Size 2 | | | 31 b | 34 c | 33 c |
| Size 3 | | | 18 a | 22 b | 20 b |
| Size 4 | largest | | 11 a | 14 a | 14 a |
| F (prob.) 2-way ANOVA | | | >0.001 | >0.001 | >0.001 |

*1 Letters indicate statistical separation (p = 0.05), Fishers protected LSD test
*2 Untreated control data not included in the analyses The relationship between the mean proportion of cracked fruit ($P_t\%$), fruit size expressed as the volume of 50 fruit V mL), the dose/concentration of glycine betaine (D ppm) and time of application, (T, where T1=1 and T2=2) was well described by the following equation.

$$P_t = -36.658 + 756.512/V - 0.00131\ D - 12.156\ T.$$

n=24.
Rsqr=0.7413.
Standard errors of 38.451, 110.35, 0.00054 and 3.137, respectively. Slopes significant at <0.001, 0.023 and <0.001, respectively.

Figure 1:
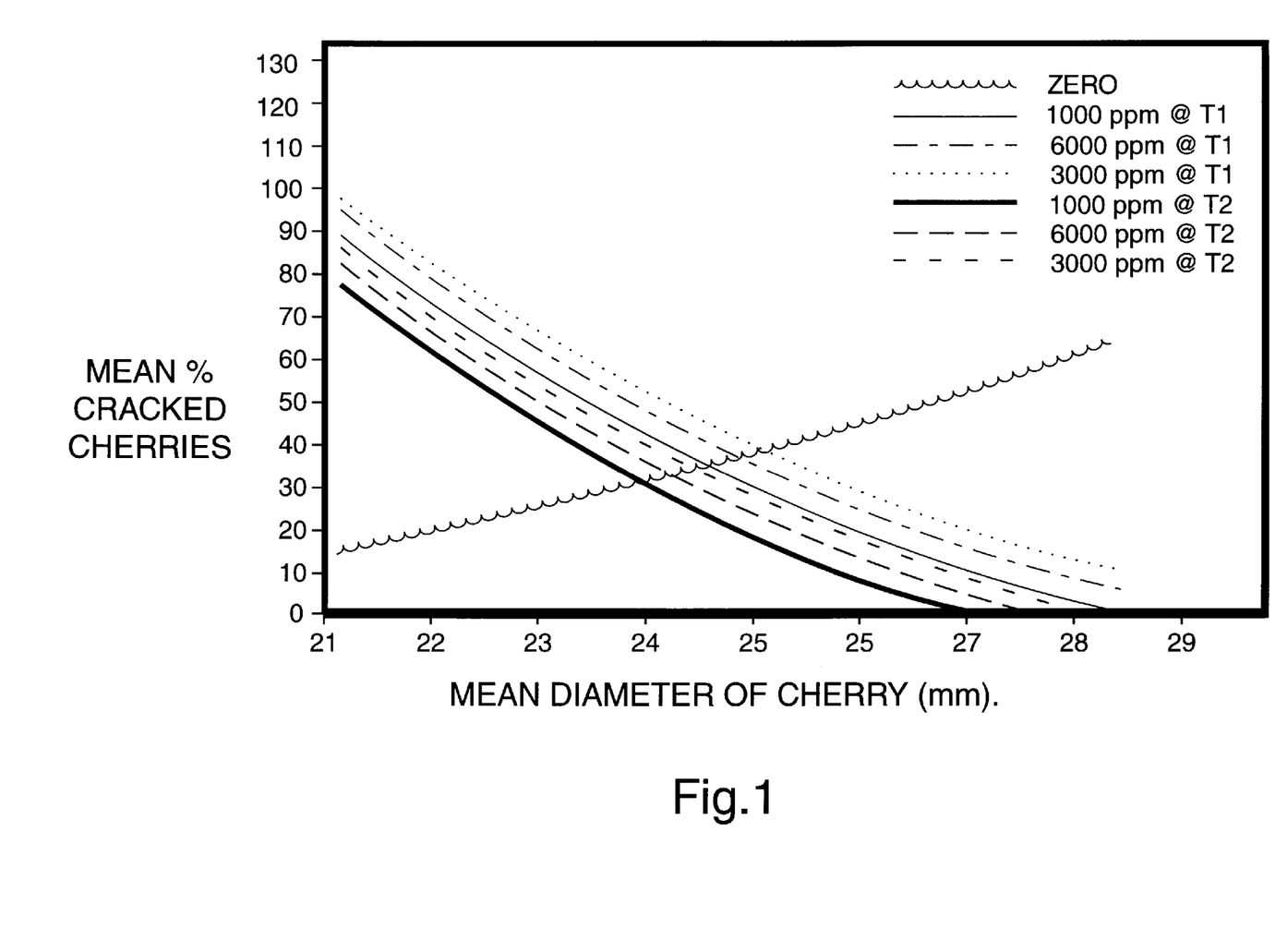
FIG. 1 is a graph showing the effect of fruit size (diameter) and the dose and timing of glycine betaine on the proportion of cracked cherries.

For the untreated control the relationship between the mean proportion of cracked fruit ($P_x\%$) and fruit size expressed as the volume of 50 fruit (V mL) was:

$$P_x = -20.403 + 0.1425\ V.$$

n=4.
Rsqr=0.9224.
Standard errors of 0.748 and 0.0292, respectively. Slope significant at 0.016. Solutions of the equations are plotted in FIG. 1, with V expressed in terms of mean diameter per cherry, assuming they are spherical.

The proportion of cherries cracked after 20 hours immersion in water decreased significantly as the dose of glycine betaine was increased and as the maturity of the cherries at application increased. But the cracking of fruit from glycine betaine treated trees decreased with increase in fruit size whilst the cracking of fruit from untreated trees increased with fruit size.

Assuming that the immersion technique predicts what will happen to fruit on the trees when conditions are favorable for cracking, treatments of glycine betaine may either decrease or increase the proportion of cracked fruit. This depends on the size of the cherries. In this trial, glycine betaine applied at 10,000 ppm at about 80% pink/red fruit, decreased cracking in fruit greater than 24 mm in diameter and increased cracking in fruit smaller than this critical diameter. It also showed that cracking decreased as the dose of glycine betaine increased and as the maturity of the fruit at application increased.

Glycine betaine appears preferably suited for use in light crops with large fruit where fruit are most likely to crack.

EXAMPLE 3

The objectives of this example are:
1. To determine the effect of foliar applications of glycine betaine on the maturity, size and finish of deciduous fruit, and
2. To determine the effect of foliar applications of glycine betaine on the tolerance of deciduous fruit trees to damage caused by two-spotted mite (*Tetranychus urticae*).

Number of Trials and Crops

On trial in pears cv Packham's Triumph and one in a cultivar of canning peach that matures about mid-season eg. Taylor Queen.

Treatments: (both crops)
A) glycine betaine at 1 kg/100 L applied at early fruit development
B) glycine betaine at 1 kg/100 L applied at early fruit development and ca 4 weeks later
C) glycine betaine at 0.5 kg/100 L applied at early fruit development and ca 4 weeks later
D) glycine betaine at 0.25 kg/100 L applied at ca 4 week intervals commencing at early fruit development
E) untreated control Adjuvant MONSOON (wetting agent) to be added to all sprays at the rate of 1–2 mL/100 L.

Application

All treatments applied to dry foliage to the point of runoff, 4 times at ca 4 week intervals.

Maturity Size and Finish

Pome fruit examination of 250 fruit per tree/plot about 1 week before harvest. Count number of fruit above the approximate control median size (using standard size gauges). Score each fruit for colour on a 2 or more point scale for colour. Score each fruit on the basis of surface area russeted using an appropriate scale. (Both colour and russet scales to be determined after an initial examination of the fruit.) Score foliage colour using an appropriate scale.

Peaches Stone hardness to be determined on 25 fruit per tree at standard time for the particular variety. One week before harvest examine 250 fruit per tree and assess as for pome fruit.

Note, with both pome fruit and peaches the fruit assessments will be conducted on 1 control per block.

Tolerance of Mites

The timing of the mite assessment will depend upon the development of the infestation. The mite infestation in each tree/plot will be scored at each application, but it is likely that one or two further inspection/scores may be required to determine the appropriate time.

The mite assessment will only be conducted if the Inspections/Scores indicate there is a response. It will entail counting motile *T. urticae* and Phytoselid mites (predators) on 24 leaves per tree; 3 inner and 3 outer at shoulder height from each quadrant. The proportion of bronzed foliage in each quadrant will then be estimated.

If glycine betaine increases the tolerance of the trees to mites then for a given infestation level, the damage in the untreated will be higher than in the treated. Twelve untreated controls are required to quantify the relationship between infestation level and damage.

From the results of this trial, it has been demonstrated that peaches have shown a significant increase in water shoot growth, which is important for growth rate and establishment of peach orchards, and that pears are growing more rapidly and are bigger in size than control Thus, it is clear that the administration of glycine betaine to pears and peaches is beneficial for both of these crops.

The described arrangement has been advanced by explanation and many modifications may be made without departing from the spirit and scope of the invention which includes every novel feature and novel combination of features herein disclosed.

Those skilled in the art will appreciate that the invention described herein is susceptible to variations and modifications other than those specifically described. It is understood that the invention includes all such variations and modifications which fall within the spirit and scope.

I claim:

1. A method of controlling stress in a growing plant to reduce surface imperfections of the skin of the fruit of the plant, comprising administering an effective amount of osmolyte regulator to the plant by foliar application such that stress induced or developing in the plant can be controlled to enhance the growth of the plant by eliminating or reducing the amount of surface imperfection, blemish or damage sustained to the skin of the fruit of the plant thereby providing a greater yield of the plant at a higher quality of product, wherein the plant is selected from the group consisting of stone fruits, pome fruits, citrus fruits, tropical fruits and nuts.

2. The method according to claim 1 in which the stone fruit is selected from the group consisting of apricots, peaches, cherries and nectarines.

3. The method according to claim 2 in which the plant is a cherry plant of the Stellar variety.

4. The method according to claim 1 in which the plant is a pear plant.

5. The method according to claim 1 in which the tropical fruits and nuts are selected from the group consisting of bananas, mangoes, macadamias and almonds.

6. The method according to claim 1 in which the osmolyte regulator is an ammonium compound, a betaine, or a betaine derivative.

7. The method according to claim 6 in which the ammonium compound is an n-methyl substituted amino acid, proline or choline.

8. The method according to claim 1 in which the betaine is selected from the group consisting of proline betaine, beta-alanine betaine, tryptophan betaine, histidine betaine and 2-mercaptohistidine betaine.

9. The method according to claim 1 in which the osmolyte regulator is a nitrogenous compatible solute selected from the group consisting of stachydrine, trigonelline and homostachydrine (pipecolate betaine).

10. The method according to claim 6 in which the osmolyte regulator is glycine, methylene glycine, dimethyl glycine, glutamic acid, $\gamma$-aminobutyric acid, trimethylamine or butyric acid.

11. The method according to claim 1 in which the osmolyte regulator is administered alone or in combination with one or more other materials.

12. The method according to claim 11 in which the other material is selected from the group consisting of wetting agents, defoliants, growth regulators, pesticides, fungicides, vegetable oil, mineral oil and nutrients.

13. The method according to claim 1 in which the stress induced or developed in the plants results from temperature, water, salinity, light, nutritional or chemical stress.

14. The method according to claim 1 in which the osmolyte regulator is administered to the plants in a concentration of up to 20,000 ppm.

15. The method according to claim 14 in which the osmolyte regulator is administered in a concentration of up to 10,000 ppm.

16. The method according to claim 15 in which the osmolyte regulator is administered in a concentration of 1,000 to 10,000 ppm.

17. The method according to claim 6 in which the osmolyte regulator is administered in a concentration of from 3,000 to 10,000 ppm.

18. The method according to claim 1 in which the dosage rate of osmolyte regulator administered to the plant is in the range of up to 10 kg/100 L.

19. The method according to claim 18 in which the dosage rate of osmolyte regulator administered to the plant is in the range of up to 5 kg/100 L.

20. The method according to claim 19 in which the dosage rate of osmolyte regulator administered to the plant is in the range of up to 2.5 kg/100 L.

21. The method according to claim 20 in which the dosage rate of osmolyte regulator administered to the plant is in the range of from 0.1 to 1 kg/100 L.

22. The method according to claim 1 in which the osmolyte regulator is applied to the leaves and fruit of the plant.

23. The method according to claim 1 in which the osmolyte regulator is applied to the plants at any time.

24. The method according to claim 23 in which the osmolyte regulator is applied to the plants after flowering the plants.

25. The method according to claim 23 in which the osmolyte regulator is applied to the plants shortly before the fruit of the plants ripens.

26. The method according to claim 23 in which the osmolyte regulator is applied to the plants just before the fruit is ready for harvesting.

27. The method according to claim 1 in which the osmolyte regulator is applied to the plants by spraying.

28. The method according to claim 27 in which the osmolyte regulator is applied to the plants by spraying an aqueous solution of the osmolyte regulator.

29. A method of controlling stress in a growing plant to reduce surface imperfections of the skins of the fruit of the plant, comprising administering an effective amount of glycine betaine to the plant by foliar application thereby controlling stress induced or developing in the plant to enhance the growth of the plant by eliminating or reducing the amount of surface imperfection, blemish or damage sustained to the skin of the fruit of the plant and providing a greater yield of the plant at a higher quality of product, wherein the plant is selected from the group consisting of stone fruits, pome fruits, citrus fruits, tropical fruits and nuts.

* * * * *

UNITED STATES PATENT AND TRADEMARK OFFICE
CERTIFICATE OF CORRECTION

PATENT NO. : 5,972,840 Page 1 of 1
DATED : October 26, 1999
INVENTOR(S) : Mottram It is certified that error appears in the above-identified patent and that said Letters Patent is hereby corrected as shown below:

<u>Title page,</u>
Item [22], PCT Filed Date should be read as -- Feb. 2, 1996 --.

Signed and Sealed this

Twenty-fifth Day of March, 2003

JAMES E. ROGAN
*Director of the United States Patent and Trademark Office*